United States Patent [19]

Liu et al.

[11] Patent Number: 4,956,442

[45] Date of Patent: Sep. 11, 1990

[54] PROCESS FOR PREPARING POLY (VINYLBENZYL ETHERS) OF POLYPHENOLS

[75] Inventors: Ming-Biann Liu; James Godschalx; Ernest Ecker; Alfred Caldecourt, all of Midland, Mich.

[73] Assignee: The Dow Chemical Company, Midland, Mich.

[21] Appl. No.: 100,067

[22] Filed: Sep. 23, 1987

[51] Int. Cl.$^5$ .................... C08G 65/40; C08G 67/02; C07C 41/00

[52] U.S. Cl. .................... 528/205; 528/211; 528/392; 568/645; 568/646; 568/647

[58] Field of Search .................... 528/205, 211, 392; 526/289, 293; 568/645, 646, 647

[56] References Cited

U.S. PATENT DOCUMENTS

| | | | |
|---|---|---|---|
| 3,058,953 | 10/1962 | McMaster | 526/289 |
| 4,116,936 | 9/1978 | Steiner | 526/286 |
| 4,180,680 | 12/1979 | Dennis | 568/647 |
| 4,707,558 | 11/1987 | Wang et al. | 568/23 |

FOREIGN PATENT DOCUMENTS 0258695 3/1988 European Pat. Off. .

*Primary Examiner*—John Kight, III
*Assistant Examiner*—P. Hampton-Hightower

[57] ABSTRACT

Poly(vinylbenzyl ethers) of polyphenols are prepared by reacting an alkali metal, alkaline earth metal, or ammonium salt of a polyphenol with a vinylbenzyl halide in a liquid reaction medium consisting essentially or a monohydric alcohol or glycol having less than 12 carbons, a polyglycol having a weight average molecular weight ranging from about 200 to about 4000, or glycerol.

Halide ion content of poly(vinylbenzyl ethers) of polyphenols prepared by the method of this invention and other methods are reduced by dissolving the ether in a solvent that dissolves no more than about 1.0 weight percent of an alkali metal, alkaline earth metal, or ammonium halide; separating the ether solution from the halide salt; and then recovering the ether from the solution.

23 Claims, No Drawings

PROCESS FOR PREPARING POLY (VINYLBENZYL ETHERS) OF POLYPHENOLS

BACKGROUND OF THE INVENTION

This invention relates to a process for preparing a poly(vinylbenzyl ether) of a polyphenol and a process for reducing the halide ion content of the prepared ether.

Poly(vinylbenzyl ethers) of polyphenols are thermoset resins disclosed in U.S. Pat. No. 4,116,936 (Steiner). They are prepared by initially dissolving a polyphenol and vinylbenzyl chloride in a solvent, e.g. acetone. The mixture is heated and a potassium hydroxide solution is added slowly. After the reaction of the mixture, the ether is first separated from precipitated potassium chloride by filtration or extraction and then separated from the remaining reaction product mixture by precipitation into methanol.

The Steiner process has four distinct disadvantages. First, the solvent employed to dissolve the polyphenol and the vinylbenzyl chloride also dissolves the prepared ether. The prepared ether must then be separated from the reaction product mixture, causing an increase in processing time and a reduction in yield. Second, the solvent reacts with the potassium hydroxide and forms undesirable byproducts that can be difficult to remove. Third, the residual chloride ion content of the prepared ether is at least 100 parts per million (ppm), typically greater than 500 ppm. The chloride ion content increases the dielectric constant and the dissipation factor of the cured resin, factors which adversely affect the performance of the resin for electronics applications. Fourth, polymer formed by the reaction of the vinyl groups with each other is difficult to remove and also adversely affects the performance of the resin.

In view of the deficiencies of the prior art, a process for preparing a poly(vinylbenzyl ether) of a polyphenol is needed which does not require a solvent that either reacts significantly with any of the reactants to form undesirable byproducts or dissolves the prepared ether. Also, a process is needed for preparing a poly(vinylbenzyl ether) of a polyphenol with a reduced halide ion content and a reduced vinyl polymer content.

SUMMARY OF THE INVENTION

The present invention is a method of preparing a poly(vinylbenzyl ether) of a polyphenol. The method comprises reacting an alkali metal, alkaline earth metal or ammonium salt of a polyphenol with a vinylbenzyl halide in a liquid reaction medium consisting essentially of a monohydric alcohol or glycol having less than 12 carbons, a polyglycol having a weight average molecular weight ranging from about 200 to about 4000, or glycerol. The separation of the prepared ether from the liquid reaction medium requires less time than the methods of the prior art without a significant loss of yield because the prepared ether is not appreciably soluble in the liquid reaction medium. The liquid reaction medium also does not react appreciably with required reactants to form undesirable byproducts.

The present invention is also a method of reducing halide ion content of a poly(vinylbenzyl ether) of a polyphenol prepared by reacting an alkali metal, alkaline earth metal or ammonium salt of a polyphenol with a vinylbenzyl halide. The method comprises dissolving the ether in a solvent that dissolves no more than about 1.0 weight percent of an alkali metal, alkaline earth metal, or ammonium halide: separating the ether solution from the halide salt: and then recovering the ether from the solution. Since the dielectric constant and the dissipation factor of the ether decrease as the halide ion content of the ether decreases, the treated ether exhibits a reduced dielectric constant and a reduced dissipation factor, properties which are critical for electronics applications.

The poly(vinylbenzyl ether) of a polyphenol prepared by the process of this invention is useful as an encapsulating or insulating resin for semiconductor devices, and for the preparation of laminates for circuit boards.

DETAILED DESCRIPTION OF THE INVENTION

Poly(vinylbenzyl ethers) of polyphenols are disclosed in U.S. Pat. No. 4,116,936 and copending U.S. Application Ser. No. 897,163, filed Aug. 15, 1986, both of which are incorporated by reference herein. Generally, the ethers are prepared from the polyphenols of bisphenol A, bisphenol S, halogenated and alkylated analogs of bisphenol A and bisphenol S, novolak resins, and polyphenols bridged by at least one polycyclic aliphatic group. Preferably, the ether is a di(vinylbenzyl ether) of a diphenol. The most preferred ether is prepared from either a meta-brominated diphenol or tetrabromobisphenol A.

The alkali metal, alkaline earth metal or ammonium salt of the polyphenol can be prepared by reacting the polyphenol with the corresponding hydroxide. In one embodiment, the polyphenol and the hydroxide are first separately dissolved in the liquid reaction medium. The hydroxide solution is then added to the polyphenol solution until the polyphenol is neutralized to the corresponding polyphenoxide. The preferred hydroxides are lithium hydroxide (sold commercially as lithium hydroxide monohydrate), sodium hydroxide, and potassium hydroxide. The most preferred hydroxide is lithium hydroxide.

The liquid reaction medium can be a monohydric alcohol or glycol having less than 12 carbons, a polyglycol having a weight average molecular weight ranging from about 200 to about 4000, or glycerol. Examples of suitable monohydric alcohols include methanol, ethanol, 1-propanol, 2-propanol, 1-butanol, and 1-pentanol. Examples of suitable glycols include ethylene glycol and propylene glycol. An example of a polyglycol within the scope of this invention includes the commercial grades of polypropylene glycol. The weight average molecular weight of the polyglycol can be determined by gel permeation chromatography. The most preferred liquid reaction mediums are methanol and ethanol.

A mixture of more than one of the liquid reaction mediums of this invention can be employed. However, it is disadvantageous to employ more than one liquid reaction medium because recycling of the medium for subsequent reactions between the polyphenoxide and the vinylbenzyl halide becomes more difficult. Likewise, a mixture of any of the liquid reaction mediums and water can be employed: however, the yield of the prepared ether decreases as the concentration of water increases. Generally, a mixture of less than about 15 weight percent water in the liquid reaction medium is acceptable, although a mixture of less than about 5 weight percent is preferred.

The amount of the vinylbenzyl halide reacted with the polyphenoxide desirably ranges from about 0.85 to about 2.0 moles of the vinylbenzyl halide for every phenoxide functionality present. Preferably, about 1.1 moles of the vinylbenzyl halide for every phenoxide functionality present is employed to maximize the conversion of the phenoxide to the ether. The reaction temperature desirably ranges from about 25° C. to about 65° C., preferably about 50° C. to about 60° C. Lower and higher temperatures than the aforementioned ranges are operable, but lower temperatures generally result in uneconomically slow rates of reactions and higher temperatures can produce undesirable polymerization. If desired, a polymerization inhibitor can be present in small amounts in the reaction medium. The most preferred vinylbenzyl halide is vinylbenzyl chloride.

The ether product precipitates from the reaction medium. In one embodiment of this invention, the ether is separated from the reaction medium in any manner known in the art. For example, the ether can be separated as a filter cake by filtering the reaction product mixture to remove the reaction medium. The filter cake can then be washed with water or an aqueous basic solution to remove halide salts, unreacted vinylbenzyl halide, and other impurities.

If lithium hydroxide is employed to neutralize the polyphenol to the corresponding polyphenoxide and a monohydric alcohol is employed as the reaction medium, then the lithium salt formed as the byproduct of the reaction between the vinylbenzyl halide and the polyphenoxide would be substantially soluble in the reaction medium. Therefore, the lithium ion content of the ether product may be reduced to acceptably low concentrations when the ether is separated from the reaction medium. If a further reduction of halide ion content is desired, or if either of lithium hydroxide or a monohydric alcohol is not employed, or if a different process is employed to prepare the ether other than the process described hereinbefore, then a reduced halide ion content can be achieved by the following method.

The halide ion content of the prepared ether can be reduced by dissolving the ether in a suitable solvent. The ether can be in the form of either a reaction product mixture obtained by reacting the polyphenoxide with the vinylbenzyl halide in the liquid reaction medium or a filter cake. A suitable solvent dissolves no more than about 1.0 weight percent of an alkali metal, alkaline earth metal, or ammonium halide, preferably no more than about 0.1 weight percent. Examples of suitable solvents are halogenated alkanes and alkenes having no more than 4 carbons, such as methylene chloride, bromochloromethane, carbon tetrachloride, chloroform, and ethylene dichloride: saturated aliphatic ketones such as acetone, methyl ethyl ketone, and methyl isobutyl ketone: dialkoxy-substituted hydrocarbons having no more than 6 carbons, such as dimethoxymethane, 1,1-dimethoxyethane, 1,2-dimethoxyethane, and 1,2-diethoxyethane: cyclic ethers such as tetrahydrofuran and dioxane and chlorobenzene. The preferred solvents are methylene chloride, bromochloromethane, chloroform and dibromomethane. The most preferred solvent is methylene chloride.

After the solvent has preferentially dissolved the ether, the halide salt can be removed from the ether solution. Since the halide salt is substantially insoluble in the solvent, the salt will remain as a precipitate which can easily be separated from the dissolved ether. This precipitate can be separated either by filtering the mixture or by washing the mixture with water or an aqueous basic solution. Not only is the halide salt substantially insoluble in the solvent, but also most polymeric impurities are substantially insoluble as well. Therefore, the halide ion content and polymer content can both be reduced by filtering the mixture.

For purposes of describing this invention, an acceptably low halide ion concentration is less than 100 ppm based on the weight of prepared ether as measured by ion chromatography, more preferably less than 50 ppm, and most preferably less than 10 ppm. An acceptably low polymer concentration is less than 1.0 percent of the weight of the prepared ether as measured by gravimetric analysis, preferably less than 0.1 percent.

After the ether solution has been separated from the halide salt, the purified ether can be recovered from the solution. In one embodiment of this invention, the purified ether is reprecipitated from solution by initially adding a second solvent in which the ether is substantially insoluble and which has a normal boiling point higher than the first solvent. The first solvent can then be removed by a variety of techniques, preferably by fractional distillation under reduced pressure. After the first solvent is removed, the purified ether can be separated from the remaining mixture by filtration. Other methods known in the art can be used to separate the purified ether from solution. The following examples illustrate but do not limit the scope of this invention.

EXAMPLE 1

236 Grams (g) (5.88 moles) of sodium hydroxide are dissolved in 3200 milliliters (ml) of methanol at 50° C. in a 10-liter, jacketed reactor equipped with a mechanical agitator, a condenser and a dropping funnel. 1595 Grams (2.94 moles) of tetrabromobisphenol A (TBBA) are dissolved in 2400 ml of methanol containing 1.3 g dinitro-o-sec-butylphenol as a polymerization inhibitor. The TBBA solution is slowly poured into the reactor to convert the diphenol to the corresponding disodium phenoxide. 987 Grams (6.47 moles) of vinylbenzyl chloride (VBC) are added to the reactor in two hours using the dropping funnel. At the end of the VBC addition, the temperature has risen to 58° C. The temperature is maintained at 58° C. for 365 minutes and then the reactor contents are cooled to 25° C. The reaction product mixture is filtered to separate the crude ether product. The crude ether product is first washed with methanol and then slurried with 50 percent methanol in water before it is filtered. The filtered product is washed with methanol, filtered, washed with methanol again and finally dried at 40° C. for 18 hours in a vacuum oven. 1974 Grams (86.5 percent yield) of a white powder are obtained with a chloride ion content of 700 pp as measured by ion chromatography.

300 Grams of the washed and filtered ether product are dissolved in 750 ml of methylene chloride. The ether solution is washed with 600 ml of water for 30 minutes. Two phases develop and the aqueous phase is removed. The procedure is repeated for two additional water washes. 1000 Milliliters of methanol are then added and the methylene chloride is stripped. The resulting mixture is filtered to removed a purified ether product which is dried at 40° C. in a vacuum oven. 291.6 Grams (84 percent yield based on TBBA) of a white powder are obtained with a residual chloride ion content of 4 ppm and a polymer content of 0.1 percent.

EXAMPLE 2

159.5 Grams (0.3 moles) of TBBA in 220 ml of methanol are added to a 2-liter, 3-necked, round-bottom flask equipped with a mechanical stirrer, a heating mantle with a temperature controller, and a dropping funnel. 23.6 Grams (0.6 moles) of sodium hydroxide are dissolved in 320 ml of methanol in a separate beaker. The sodium hydroxide solution is gradually added to the TBBA solution in the reactor to convert the diphenol to the corresponding disodium phenoxide. When the temperature reaches 35° C., 98.7 g (0.65 moles) of VBC containing 0.13 g of dinitro-o-sec-butylphenol as a polymerization inhibitor is added to the reactor. The reaction mixture is heated at 60° C. for 225 minutes and is then allowed to cool to 40° C.

736 Grams of methylene chloride are added to the reaction product mixture. The crude ether product, which has precipitated from the mixture, dissolves in 5 minutes. 430 Milliliters of water are added and the contents are stirred for 10 minutes to extract the sodium chloride salt. After two phases develop, the aqueous phase is removed. The procedure is repeated twice with 450 ml of water. The methylene chloride phase is then transferred to a separate beaker. 140 Grams of the methylene chloride layer are added to 586 g of methanol in a separate flask which is attached to a rotary vacuum evaporator. Vacuum is applied to strip the methylene chloride at a temperature ranging from about 20° to about 30° C. The stripping is repeated for every 140 g of the methylene chloride layer until all of the methylene chloride layer is processed. The remaining mixture of purified ether product in methanol is filtered and dried at 40° C. in a vacuum oven for 18 hours. 203.5 Grams (89 percent yield based on TBBA) of a white powder are obtained with less than 2 ppm chloride ion content as measured by ion chromatography and 0.5 percent polymer as measured by gravimetric analysis.

EXAMPLE 3

25.2 Grams (0.600 moles) of lithium hydroxide monohydrate are dissolved in 1000 ml of methanol and added to a 5-liter, round-bottom reactor equipped with a mechanical agitator, a condenser, a dropping funnel, a heating mantle and a thermometer. 159.5 Grams (0.293 moles) of TBBA are dissolved in 325 ml of methanol in a separate flask. The TBBA solution is poured into the reactor over a few minutes and heated for about 2 hours at 40° C. to convert the diphenol to the corresponding dilithium phenoxide. 0.16 Grams ionol (2,6-di(t-butyl)-4-methylphenol) is added to the reactor as a polymerization inhibitor. After formation of the dilithium phenoxide, 98.7 g (0.647 moles) of VBC are added to the reaction mixture in 15 minutes through the dropping funnel. As the VBC is added, the reaction mixture is slowly heated to a temperature ranging from about 56° C. to about 60° C. The temperature of the reaction mixture is maintained at this temperature for an additional 270 minutes and then cooled to room temperature. The resulting reaction product mixture is filtered and the white solid filtrate is washed with 1000 ml of methanol. The treated solid is then dried in a vacuum oven. 187 Grams (82 percent yield based on TBBA) of a white powder are obtained with a chloride ion content of 17 ppm as measured by ion chromatography.

Upon repeating any of Examples 1, 2 or 3 with other polyphenols, similar excellent results are obtained.

What is claimed is:

1. A method of preparing a poly(vinylbenzyl ether) comprising the step of reacting an alkali metal, alkaline earth metal, or ammonium salt of a polyphenol with a vinylbenzyl halide in an essentially non-aqueous liquid reaction medium consisting essentially of a monohydric alcohol or glycol having less than 12 carbon atoms, a polyglycol having a weight average molecular weight ranging from about 200 to about 4000, or glycerol, said vinyl benzyl halide being in stoichiometric excess relative to the salt of the polyphenol.

2. The method of claim 1 wherein the ether prepared is a di(vinylbenzyl) ether of a diphenol.

3. The method of claim 2 wherein the ether prepared is derived from a meta-brominated diphenol.

4. The method of claim 2 wherein the ether prepared is derived from tetrabromobisphenol A.

5. The method of claim 1 wherein the vinylbenzyl halide is vinylbenzyl chloride.

6. The method of claim 1 wherein the monohydric alcohol is selected from the group consisting of methanol, ethanol, 1-propanol, 2-propanol, 1-butanol, and 1-pentanol.

7. The method of claim 1 wherein the glycol is selected from the group consisting of ethylene glycol and propylene glycol.

8. The method of claim 1 wherein the polyglycol is polypropylene glycol.

9. The method of claim 6 wherein the monohydric alcohol is selected from the group consisting of methanol and ethanol.

10. The method of claim 9 wherein the alkali metal salt of the polyphenol is prepared by reacting a polyphenol with lithium hydroxide, sodium hydroxide, or potassium hydroxide.

11. The method of claim 10 wherein the alkali metal salt of the polyphenol is prepared by reacting a polyphenol with lithium hydroxide.

12. The method of claim 1 further comprising the steps of:
    (a) dissolving the prepared ether in a solvent that dissolves no more than about 1.0 weight percent of an alkali metal, alkaline earth metal, or ammonium halide:
    (b) separating the ether solution from the halide salt: and then
    (c) recovering the ether from the solution thereby reducing the halide ion content of the prepared ether.

13. The method of claim 12 wherein the solvent dissolves no more than about 0.1 weight percent of an alkali metal, alkaline earth metal, or ammonium halide.

14. The method of claim 12 wherein the solvent is selected from the group consisting of a halogenated alkane or alkene having no more than 4 carbons, a saturated aliphatic ketone, a dialkoxy-substituted hydrocarbon having no more than 6 carbons, a cyclic ether, and chlorobenzene.

15. The method of claim 14 wherein the solvent is selected from the group consisting of methylene chloride, bromochloromethane, chloroform, and dibromomethane.

16. The method of claim 15 wherein the solvent is methylene chloride.

17. A method of reducing halide ion content of a poly(vinylbenzyl ether) of a polyphenol prepared by reacting an alkali metal, alkaline earth metal or ammonium salt of a polyphenol with a vinylbenzyl halide, comprising the steps of:

(a) dissolving the ether in a solvent that dissolves no more than about 1.0 weight percent of an alkali metal, alkaline earth metal, or ammonium halide:
(b) separating the ether solution from the halide salt: and then
(c) recovering the ether from the solution.

18. The method of claim 17 wherein the solvent dissolves no more than about 0.1 weight percent of an alkali metal, alkaline earth metal, or ammonium halide.

19. The method of claim 17 wherein the solvent is selected from the group consisting of a halogenated alkane or alkene having no more than 4 carbons, a saturated aliphatic ketone, a dialkoxy-substituted hydrocarbon having no more than 6 carbons, a cyclic ether, and chlorobenzene.

20. The method of claim 19 wherein the solvent is selected from the group consisting of methylene chloride, bromochloromethane, chloroform, and dibromomethane.

21. The method of claim 20 wherein the solvent is methylene chloride.

22. The method of claim 1 wherein the liquid reaction medium comprises less than 5 weight percent water.

23. The method of claim 1 wherein said polyphenol is tetrabromobisphenol A.

* * * * *